(12) United States Patent
Lee

(10) Patent No.: US 12,207,991 B2
(45) Date of Patent: Jan. 28, 2025

(54) MODIFIED MEMBER FOR PREVENTING BEDSORE

(71) Applicant: Keun Cheol Lee, Busan (KR)

(72) Inventor: Keun Cheol Lee, Busan (KR)

( * ) Notice: Subject to any disclaimer, the term of this patent is extended or adjusted under 35 U.S.C. 154(b) by 69 days.

(21) Appl. No.: 17/262,736

(22) PCT Filed: Dec. 13, 2019

(86) PCT No.: PCT/KR2019/017751
§ 371 (c)(1),
(2) Date: Jan. 24, 2021

(87) PCT Pub. No.: WO2020/213810
PCT Pub. Date: Oct. 22, 2020

(65) Prior Publication Data
US 2022/0023104 A1 Jan. 27, 2022

(30) Foreign Application Priority Data
Apr. 18, 2019 (KR) .......................... 10-2019-0045574

(51) Int. Cl.
*A61F 13/0203* (2024.01)
*A61F 13/00* (2024.01)

(52) U.S. Cl.
CPC ...................... *A61F 13/0213* (2013.01); *A61F 2013/00404* (2013.01); *A61F 2013/0057* (2013.01); *A61F 2013/00919* (2013.01)

(58) Field of Classification Search
CPC ............... A61F 13/00; A61F 13/00021; A61F 13/00085; A61F 13/0246; A61F 13/0253;
(Continued)

(56) References Cited

U.S. PATENT DOCUMENTS

| 4,399,816 A | 8/1983 | Spangler |
| 4,470,410 A | 9/1984 | Elliott |

(Continued)

FOREIGN PATENT DOCUMENTS

| CN | 101869517 A | 10/2010 |
| CN | 102274574 A | 12/2011 |

(Continued)

OTHER PUBLICATIONS

Machine translation of KR101923986B1 (Year: 2019).*

(Continued)

*Primary Examiner* — Caitlin A Carreiro
(74) *Attorney, Agent, or Firm* — ANTONIO HA & U.S. PATENT, LLC

(57) ABSTRACT

The present invention relates to a modified member for preventing bedsores, which includes a stacked body composed of: a pad layer formed from synthetic resin foam and hydrocolloid or hydrogel, a cover layer which is integrally stacked on the outer surface of the pad layer, and a pressure-sensitive adhesive layer formed on the inner surface of the cover layer and having a pressure-sensitive adhesive, in which the cover layer includes an opening penetratingly formed at a central portion thereof to allow the patient's skin to be observed therethrough, thereby preventing bedsores from developing between the central part of the buttock and the anus and at bilateral femoral puncture sites of patients who have been bedridden for a long time.

3 Claims, 9 Drawing Sheets

(58) Field of Classification Search
CPC .............. A61F 13/0213; A61F 13/022; A61F 13/024; A61F 13/0259; A61F 13/069; A61F 13/06; A61F 13/063; A61F 2013/00259; A61F 5/443
USPC .................... 602/41, 43, 52, 54, 57, 58, 59; 128/889–890, 892–894

See application file for complete search history.

(56) References Cited

U.S. PATENT DOCUMENTS

| | | | |
|---|---|---|---|
| 5,086,763 | A | 2/1992 | Hathman |
| 2002/0169405 | A1* | 11/2002 | Roberts ............... A61F 13/023 602/56 |
| 2007/0043316 | A1 | 2/2007 | Carlson et al. |
| 2015/0173758 | A1 | 6/2015 | Barcroft et al. |
| 2017/0090584 | A1 | 3/2017 | Tang et al. |

FOREIGN PATENT DOCUMENTS

| | | |
|---|---|---|
| CN | 205626275 U | 10/2016 |
| CN | 208372018 U | 1/2019 |
| CN | 109310529 A | 2/2019 |
| CN | 208582595 U | 3/2019 |
| JP | H02-74252 | 3/1990 |
| JP | H5-068692 | 3/1993 |
| JP | H08-033674 A | 2/1996 |
| JP | 2001-511396 A | 8/2001 |
| JP | 2003-033383 A | 2/2003 |
| JP | 2006-311913 A | 2/2003 |
| JP | 3614371 B2 | 1/2005 |
| JP | 2008-054818 A | 3/2008 |
| JP | 4815183 B2 | 11/2011 |
| JP | 5734242 B2 | 6/2015 |
| KR | 10-1426740 | 8/2014 |
| KR | 10-2015-0022673 | 3/2015 |
| KR | 10-2016-0034430 | 3/2016 |
| KR | 10-1660215 | 9/2016 |
| KR | 10-2016-0118877 | 10/2016 |
| KR | 10-2017-0072187 | 6/2017 |
| KR | 10-1914781 | 11/2018 |
| KR | 10-1923986 | 2/2019 |
| KR | 101923986 B1 * | 2/2019 |
| KR | 10-2022433 | 11/2019 |
| WO | WO-2007071642 A1 * | 6/2007 .......... A61N 1/0468 |
| WO | WO2018026142 A1 | 2/2018 |

OTHER PUBLICATIONS

English Specification of CN101869517A.
English Specification of CN102274574A.
English Specification of CN109310529A.
English Specification of CN205626275U.
English Specification of CN208372018U.
English Specification of CN208582595U.
English Specification of JPH02-74252.
English Specification of JPH08-033674A.
English Specification of JP2001-511396A.
English Specification of JP2003-033383A.
English Specification of JP2006-311913A.
English Specification of JP2008-054818A.
English Specification of JP3614371B2.
English Specification of JP4815183B2.
English Specification of JP5734242B2.
English Specification of 10-1660215.
English Specification of 10-1426740.
English Specification of 10-1923986.
English Specification of 10-2015-0022673.
English Specification of 10-2016-0034430.
English Specification of 10-2016-0118877.
English Specification of 10-2017-0072187.
English Specification of WO2018026142A1.
English Specification of 10-2022433.
English Specification of 10-1914781.
English Specification of JPH5-068692.

* cited by examiner (a)

(b)

MODIFIED MEMBER FOR PREVENTING BEDSORE

TECHNICAL FIELD

The present invention relates to a modified member for preventing bedsores, and more particularly to a modified member for preventing bedsores from developing due to either exudate generated from inflamed skin or wounds between the central part of the buttock and the anus and at bilateral femoral puncture sites of patients who have been bedridden for a long time, or excrement such as urine or feces permeating the modified member, wherein the modified member includes a lid cover disposed on an upper outer surface of a lid and having an area larger than that of the lid, so that the lid can be opened, closed and replaced easily, and thus the patients can maintain comfortable bed lives and prevent the development of bedsores.

BACKGROUND ART

In general, bedsores or pressure ulcers develop well in patients without consciousness recovery, patients who are immobile due to cranial or spinal nerve damage or critically ill patients, patients with systemic breakdown, and elderly people or patients admitted to long-term care hospitals (LTCHs). For such patients, constant or repetitive pressure is applied to specific parts of their bodies when they continue to sit or lie down in fixed postures so that although damage is caused to their skins and underlying tissues due to blood circulation disorders, they do not feel unpleasant sensations. Even if the patients feel any unpleasant sensations, they have no energy to change their postures by themselves, leading to a possibility for bedsores to develop or get worse.

In particular, for the sake of patients who have been bedridden for a long time, various kinds of bedsore prevention diaper covers for receiving excrement such as urine and feces are developed and their related patent applications are filed in Korea and foreign countries.

A review of prior patent documents relating to such diaper covers will be made hereinafter.

A diaper cover for preventing bedsores, which is disclosed in Japanese Patent No. 3614371 (issued on Jan. 26, 2005) is configured such that a stacked body 5 in which a waterproof sheet 3 and a pad 4 having excellent hygroscopicity and air-permeability are overlapped with each other is disposed on the inner surface of a diaper cover 1, and the waterproof sheet 3 is positioned at an inner stopping point of the diaper cover 1 so that urine permeates between the waterproof sheet 3 and the diaper cover 1 as shown in FIG. 1. A diaper disclosed in Japanese Patent No. 5734242 (issued on Jun. 17, 2015) is configured such that it is provided with a diaper main body 10 including a waterproof sheet 12 disposed at an outer side of a water-absorbent sheet 11 and having an opening 18 formed at a portion thereof where the anus, an excretory orifice is positioned, and with an excrement collecting container 20 disposed below the opening 18 and having defined therein a space where urine and feces are collected as shown in FIG. 2.

However, even though the diaper cover for preventing bedsores disclosed in Japanese Patent No. 3614371 (issued on Jan. 26, 2005) absorbs a patient's urine through the pad 4 and the diaper disclosed in Japanese Patent No. 5734242 (issued on Jun. 17, 2015) discharges excrement such as urine and feces released from a patient's body to the excrement collecting container 20 through the opening 18 formed on the diaper main body 10, the excrements are not completely disposed of within the diaper. Thus, when the patients' excrements leaded out of the diapers frequently come into close contact with their sacral regions where bedsores are apt to occur, there is a problem in that bedsores are highly likely to develop.

Meanwhile, in an attempt to solve the above-described problem, Japanese Patent No. 4815183 (issued on November 16) discloses a bedsore therapeutic sheet. A disposable diaper 1 to which the bedsore therapeutic sheet is applied is well-known in the art. The disposable diaper 1 consists of a liquid-permeable top sheet 2 to which a bedsore therapeutic sheet 41 is adhered and a liquid-impermeable back sheet 3 as shown in FIG. 3(a). The bedsore therapeutic sheet 41 (denoted by reference numeral 21 in FIG. 3(b)) is configured such that the edges of a liquid-permeable sheet material 22 having liquid passage holes 23 formed thereon are formed convexly from one-side surface 26 of the liquid-permeable sheet material 22 as shown in FIG. 3(b). However, the bedsore therapeutic sheet disclosed in the above-mentioned Japanese Patent No. 4815183 (issued on November 16) is intended to inhibit the volatilization of a medication applied to a bedsore site but not to absorb the medication, and to discharge pus emitted from the bedsore affected area through the liquid passage holes, for the purpose of treating bedsore that has already developed rather than preventing the development of bedsore.

Therefore, the present inventor has developed a member for preventing bedsores, which has a structure as shown in FIG. 4 in order to solve the above-described problems, and has been granted a patent for the member for preventing bedsores as disclosed in Korean Patent No. 10-1923986 (issued on Feb. 22, 2019), but the present inventor has modified the member for preventing bedsores of Korean Patent No. 10-1923986 to offer better convenience of use to actual patients, thereby completing the present invention.

DISCLOSURE OF INVENTION

Technical Problem

Accordingly, the present invention has been made in order to solve the above-described problems occurring in the prior art, and it is an object of the present invention is to provide a modified member for preventing bedsores in which a lid cover having an area larger than that of a lid is disposed on the upper outer surface of the lid, the lid cover includes a structure in which a pressure-sensitive adhesive layer, a release material layer, and a protective layer are stacked upwards in order, and a nonwoven fabric of the release material layer is adhered to a cover layer of a synthetic resin film that is an upper layer of a stacked body by means of the pressure-sensitive adhesive layer of the lid cover, so that easy attachment and detachment between the cover layer and the release material layer is achieved, making it easy to open/close the lid.

Another object of the present invention is to provide a modified member for preventing bedsores in which when a lid and a pad layer are contaminated due to either exudate generated from inflamed skin or wounds between the central part of the buttock and the anus and at bilateral femoral puncture sites of a patient who has been bedridden for a long time, or excreta such as urine or feces permeating the modified member, the lid can be easily replaced with new one and can be easily opened/closed anytime to allow an affected part of the patient's skin to be observed with naked eyes or to enable medical treatments such as applying powder or wound ointment on the affected part of the skin and the like to promote wound healing, so that the patient can maintain a comfortable bed live and prevent the development of bedsores.

Still another object of the present invention is to provide a modified member for preventing bedsores in which when it is adhered to a skin site between the central part of the buttock and the anus and bilateral femoral puncture sites where bedsore is apt to occur, a patient's excrement such as urine and feces does not permeate the skin site, in which an affected part of the patient's skin can be observed with naked eyes through an opening formed on a cover layer, and in which a pad is stuck to a skin site that is applied with pressure that is one of key causes of bedsore development to reduce the pressure, thereby preventing the development of bedsores.

Yet another object of the present invention is to provide a modified member for preventing bedsores in which in addition to the use of the modified member for prevention of bedsores, even in the treatment of skin trauma such as common wounds and burns, the treatment state of the skin trauma can be observed with naked eyes by opening a lid of an opening formed at the central portion of a cover layer using the modified member so that the frequency of unnecessary treatments can be reduced, and only an opening/closing element (i.e., the lid) can be easily replaced with new one without completely removing the modified member so that the use of the member for medical treatment can be reduced, thereby ensuring economic efficiency.

Technical Solution

To achieve the above objects, the present invention provides a modified member for preventing bedsores, which includes a stacked body composed of: a pad layer 10 of a synthetic resin film formed in a sheet type from synthetic resin foam and hydrocolloid or hydrogel, so as to come into direct contact with a patient's skin; a cover layer 20 of a synthetic resin film, which is integrally stacked on the outer surface of the pad layer 10; and a pressure-sensitive adhesive layer 30 formed on the inner surface of the cover layer 20 and having a pressure-sensitive adhesive applied thereon, wherein the cover layer 20 includesmodified member including: an opening 50 penetratingly formed at a central portion thereof to allow an affected part of the patient's skin to be observed with naked eyes therethrough; and wherein the modified member further includes a lid 40 disposed at the opening to correspond to the shape of the opening 50 so that the lid can be opened/closed relative to the opening 50 by press-fit engagement; and a lid cover 90 disposed on the upper outer surface of the lid 40 and having an area larger than that of the lid.

In addition, the lid cover 90 may include a structure in which a pressure-sensitive adhesive layer 91, a release material layer 92, and a protective layer 93 are stacked upwards in order, so that the release material layer 92 is adhered to the cover layer 20 that is an upper layer of the stacked body by means of the pressure-sensitive adhesive layer 91 of the lid cover 90.

Further, the length and width of the cover layer 20 may be larger than that of the pad layer 10 of a synthetic resin film formed in a sheet type from synthetic resin foam and hydrocolloid or hydrogel, and the cover layer 20 may be stacked on the pad layer 10 in such a manner that the pad layer 10 is positioned around the central portion of the cover layer 20. The modified member 100 for preventing bedsores may include either an upper release paper 60 and a lower release paper 70, which are respectively stacked on both outer surfaces thereof, or the lower release paper 70 stacked on one outer surface thereof. The pad layer (10) may be obtained by impregnating the synthetic resin foam with hydrocolloid or hydrogel.

Advantageous Effects

The modified member for preventing bedsores according to the present invention has effects in that when it is adhered to a skin site between the central part of the buttock and the anus where bedsore is apt to occur, a patient's excrement such as urine and feces does not permeate the skin site, in that the modified member is stuck to a portion of a skin site that is applied with pressure serves as a pad to reduce the pressure, and in that an affected part of the patient's skin can be observed with naked eyes through the opening formed on the cover layer, thereby preventing the development of bedsores.

In addition, the modified member for preventing bedsores according to the present invention has effects in that the pad layer of a synthetic resin film formed in a sheet type from synthetic resin foam and hydrocolloid or hydrogel is used in an aseptic state or imparts a wound healing effect by impregnating the synthetic resin foam with hydrocolloid or hydrogel, so that even when bedsores develop, it can be treated, and the treatment state of the bedsores can be observed with naked eyes by opening the lid of the opening formed at the central portion of the cover layer.

Further, the modified member for preventing bedsores according to the present invention has effects in that the lid cover having an area larger than that of a lid is disposed on the upper outer surface of the lid, the lid cover includes a structure in which the pressure-sensitive adhesive layer, the release material layer, and the protective layer are stacked upwards in order, and a nonwoven fabric of the release material layer is adhered to the cover layer of a synthetic resin film that is an upper layer of the stacked body by means of the pressure-sensitive adhesive layer of the lid cover, so that easy attachment and detachment between the cover layer and the release material layer is achieved, making it easy to open/close the lid.

Besides, the modified member for preventing bedsores according to the present invention has effects in that when a lid and a pad layer are contaminated due to either exudate generated from inflamed skin or wounds between the central part of the buttock and the anus and at bilateral femoral puncture sites of a patient who has been bedridden for a long time, or excreta such as urine or feces permeating the modified member, the lid can be easily replaced with new one and can be easily opened/closed anytime to allow an affected part of the patient's skin to be observed with naked eyes or to enable medical treatments such as applying powder or wound ointment on the affected part of the skin and the like to promote wound healing, so that the patient can maintain a comfortable bed live and prevent the development of bedsores.

Furthermore, the modified member for preventing bedsores according to the present invention has effects in that in addition to the use of the modified member for prevention of bedsores, even in the treatment of skin trauma such as common wounds and burns, the treatment state of the skin trauma can be observed with naked eyes by opening the lid of the opening formed at the central portion of the cover layer using the modified member so that the frequency of unnecessary treatments can be reduced, and only the opening/closing element (i.e., the lid) can be easily replaced with new one without completely removing the modified member so that the use of the member for medical treatment can be reduced, thereby ensuring economic efficiency.

BRIEF DESCRIPTION OF THE DRAWINGS

The above and other objects, features and advantages of the present invention will be more apparent from the following detailed description of the preferred embodiments of the invention in conjunction with the accompanying drawings, in which.

BEST MODE FOR CARRYING OUT THE INVENTION

Figure 1:
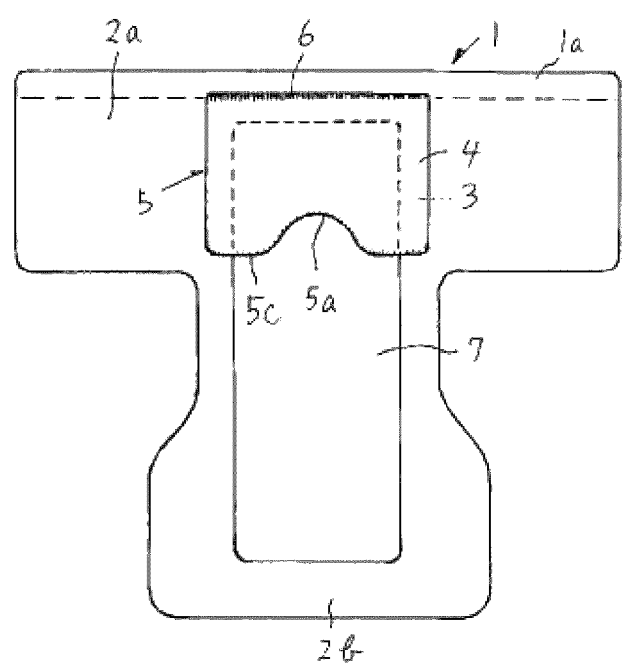
FIGS. 1 and 2 are top plan and perspective views showing a diaper cover for preventing bedsores and a diaper cover according to the prior art.
Figure 2:
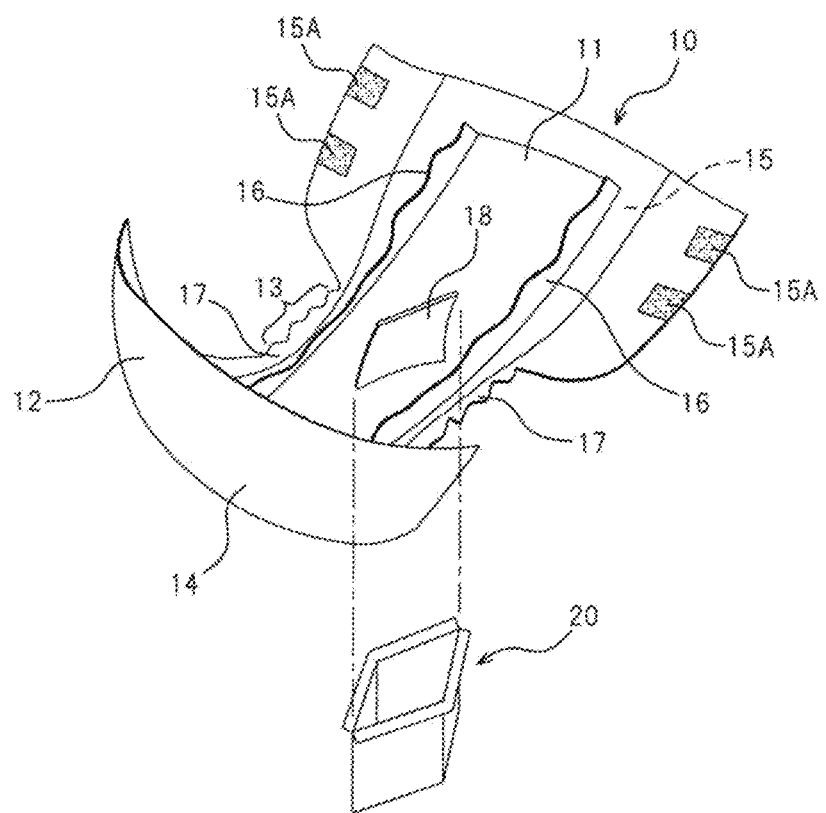
Figure 3:
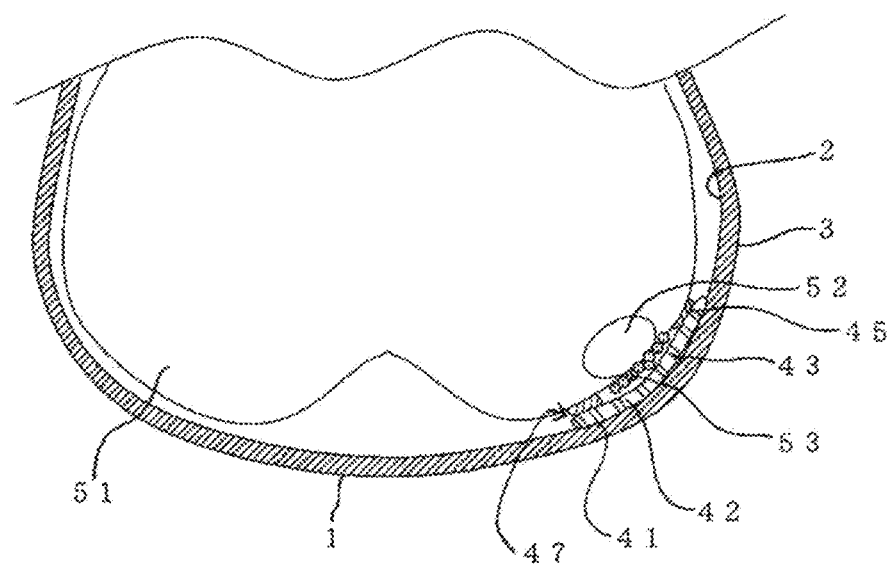
FIG. 3 is a cross-sectional view showing a bedsore therapeutic sheet according to the prior art.
Figure 3:
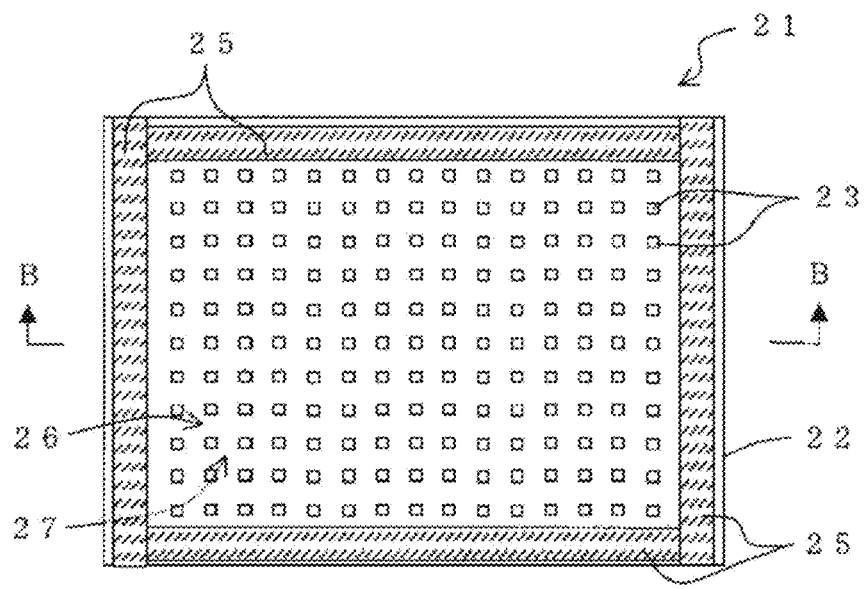

Hereinafter, a preferred embodiment of the present invention will be described in further detail with reference to the accompanying drawings.

In FIGS. 5 to 9, elements performing the same function are denoted by identical reference numerals. In the meantime, in the detailed description and the accompanying drawings, illustration and explanation on the detailed technical construction and operation of elements, which have no direct connection with the technical features of the present invention, will be omitted, and only the technical constructions directly related with the present invention will be briefly illustrated and explained.

For reference, in the phrase 'modified member for preventing bedsores' as used herein, 'for preventing bedsores' means the use of the modified member for preventing bedsores from occurring in a patient's skin, and has the same meaning as 'for prophylaxis of bedsore'.

In addition, in describing a modified member 100 for preventing bedsores according to the present invention, when describing each layer of a stacked body of the modified member 100, the term 'inner surface' refers to a face of a side of a pad layer, which comes into direct contact with a patient's skin, and 'outer surface' refers to a face opposed to the 'inner surface'.

Referring to FIGS. 5 to 9, the modified member 100 for preventing bedsores according to the present invention includes a stacked body composed of: a pad layer 10 of a synthetic resin film formed in a sheet type from synthetic resin foam and hydrocolloid or hydrogel, so as to come into direct contact with a patient's skin; a cover layer 20 of a synthetic resin film, which is integrally stacked on the outer surface of the pad layer 10; and a pressure-sensitive adhesive layer 30 formed on the inner surface of the cover layer 20 and having a pressure-sensitive adhesive applied thereon. The cover layer 20 includes: an opening 50 penetratingly formed at a central portion thereof to allow an affected part of the patient's skin to be observed with naked eyes therethrough. The modified member 100 for preventing bedsores further includes: a lid 40 disposed at the opening 50 to correspond to the shape of the opening 50 so that the lid can be opened/closed relative to the opening 50 by press-fit engagement; and a lid cover 90 disposed on the upper outer surface of the lid 40 and having an area larger than that of the lid.

Typically, for a patient who has been bedridden for a long time, when a physical pressure is applied to between the central part of the buttock and the anus and to bilateral femoral puncture sites as his or her excrement that leaked out of a diaper cover permeates both between the central part of the buttock and the anus and the bilateral femoral puncture sites, the skin and its subcutaneous tissue is damaged while being inflamed, leading to the development of a pressure ulcer.

Figure 4:
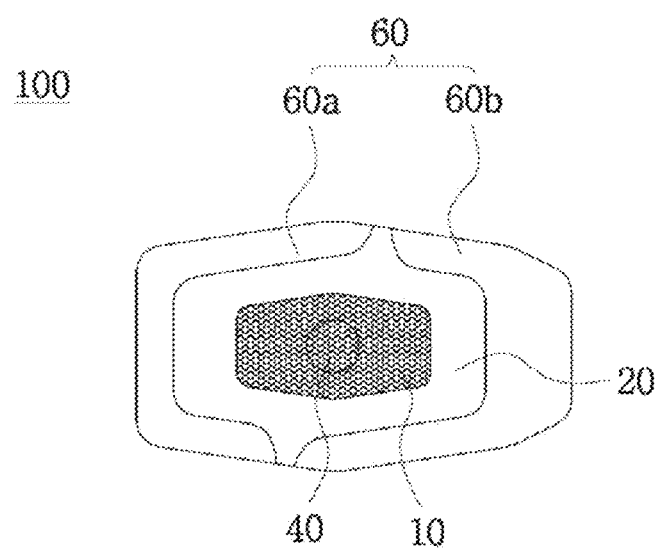
FIG. 4 is a top plan view showing a member for preventing bedsores according to the prior art (i.e., Korean Patent No. 10-1923986 (issued on Feb. 22, 2019))

The member for preventing bedsores of Korean Patent No. 10-1923986 (issued on Feb. 22, 2019) which the present invention has developed and for which the present inventor has been granted a patent is characterized in that the member 100 for preventing bedsores is first adhered to a skin site where bedsores are apt to occur before allowing a patient bedridden for a long time to wear a disposable diaper, and then the patient is allowed to wear the disposable diaper, so that excrement such as urine and feces excreted from the patient's body is prevented from permeating a skin site between the central part of the buttock and the anus where bedsore is apt to occur, thereby avoiding the development of bedsores. However, the above-mentioned member for preventing bedsores of Korean Patent No. 10-1923986 has a structure as shown in FIG. 4, in which a lid 4 is not opened/closed easily, which makes it difficult to observe the patient's affected part. In particular, when a large amount of exudate is generated from inflamed skin or wounds at the patient's buttock, the pad layer 10 has a limitation in absorbing the large amount of exudate, thereby causing a problem in that although the pad layer 10 needs to be frequently replaced with new one, it is not more easily replaced with new one.

Thus, the modified member for preventing bedsores according to the present invention is characterized in that the lid cover 90 includes a structure in which a pressure-sensitive adhesive layer 91, a release material layer 92, and a protective layer 93 are stacked upwards in order, so that the release material layer 92 is adhered to the cover layer 20 that is an upper layer of the stacked body by means of the pressure-sensitive adhesive layer 91 of the lid cover 90 by modifying the structure of the member for preventing bedsores disclosed in the above-mentioned Korean Patent No. 10-1923986 (issued on Feb. 22, 2019)

The lid cover 90 may include a knob 90a formed at one side or both sides thereof to facilitate the opening/closing of the lid 40 relative to the opening 50.

In the present invention, a pressure-sensitive adhesive that can be used for the pressure-sensitive adhesive layer 91 is preferably a polyurethane-based pressure sensitive adhesive or a silicon pressure sensitive adhesive which is harmless to the human body. In addition to the limited examples of the pressure-sensitive adhesive, any pressure sensitive adhesive may be used without limitation as long as it is a pressure sensitive adhesive that has the physical properties equivalent to those of the above-enumerated pressure sensitive adhesives and is harmless to the human body.

A material used for the release material layer 92 is preferably selected from among a nonwoven fabric, a natural fiber fabric, a synthetic fiber fabric, a natural rubber material, and a synthetic rubber material. In addition to the limited examples of the release material, any material may be used without limitation as long as it is a material that has the physical properties equivalent to those of the above-enumerated release materials and is harmless to the human body.

A material used for the protective layer 93 may be selected from among various synthetic resin materials such as polyurethane, polyethylene, and polypropylen, but in addition to the limited examples of the material, any material may be used without limitation as long as it is a material that has the physical properties equivalent to those of the above-enumerated materials and is harmless to the human body.

Thus, the present invention is a modification to the conventional member for preventing bedsores disclosed in Korean Patent No. 10-1923986 (issued on Feb. 22, 2019). According to the modified member for preventing bedsores of the present invention as described above, the lid cover having an area larger than that of the lid is disposed on the upper outer surface of the lid, the lid cover includes a structure in which the pressure-sensitive adhesive layer, the release material layer, and the protective layer are stacked upwards in order, and the nonwoven fabric of the release material layer is adhered to the cover layer of a synthetic resin film that is an upper layer of the stacked body by means of the pressure-sensitive adhesive layer of the lid cove), so that easy attachment and detachment between the cover layer and the release material layer is achieved, making it easy to open/close the lid. In addition, the lid and the pad layer are contaminated due to either exudate generated from inflamed skin or wounds between the central part of the buttock and the anus and at bilateral femoral puncture sites of a patient who has been bedridden for a long time, or excreta such as urine or feces permeating the modified member, the lid can be easily replaced with new one and can be easily opened/closed anytime to allow an affected part of the patient's skin to be observed with naked eyes or to enable medical treatments such as applying powder or wound ointment on the affected part of the skin and the like to promote wound healing, so that the patient can maintain a comfortable bed live and prevent the development of bedsores.

Furthermore, according to the modified member for preventing bedsores according to the present invention, in addition to the use of the modified member for prevention of bedsores, even in the treatment of skin trauma such as common wounds and burns, the treatment state of the skin trauma can be observed with naked eyes by opening the lid of the opening formed at the central portion of the cover layer using the modified member so that the frequency of unnecessary treatments can be reduced, and only the opening/closing element (i.e., the lid) can be easily replaced with new one without completely removing the modified member so that the use of the member for medical treatment can be reduced, thereby ensuring economic efficiency.

The pad layer 10 of a synthetic resin film formed in a sheet type from synthetic resin foam and hydrocolloid or hydrogel is a layer that comes into direct contact with a patient's skin site where bedsores are apt to occur. The pad layer 10 serves to absorb sweat, wastes or blood discharged from the skin site where bedsores occur. In the present invention, as a material for pad layer 10, a sterilized material is used to prevent the patient's skin from being contaminated.

The pad layer 10 that is used in the present invention is in the form of a synthetic resin film formed in a sheet type from foam obtained by foaming synthetic resin, and hydrocolloid or hydrogel. A material for the foam and the synthetic resin film that can be used in the present invention may be various synthetic resin materials such as polyurethane, polyethylene and polypropylene, but is most preferably polyurethane.

In addition, the pad layer 10 may be used by impregnating the synthetic resin foam with hydrocolloid (hydrophilic colloid) or hydrogel. Hydrocolloid acts to absorb sweat, wastes or blood discharged from a bedsore site to form hydrogel so that development of bedsores can be prevented.

Hydrocolloid (hydrophilic colloid) that can be used in the present invention may be one or more selected from among collagen, hydroxyethylcellulose, mthylcellulose, ethylcellulose, and carboxymethylcelluse sodium. In addition to the limited examples of the hydrocolloid, any material may be used without limitation as long as it is a material that has the physical properties equivalent to those of the above-enumerated materials.

Thus, in the modified member for preventing bedsores according to the present invention, the pad layer of a synthetic resin film formed in a sheet type from synthetic resin foam and hydrocolloid or hydrogel is used in an aseptic state or imparts a wound healing effect by impregnating the synthetic resin foam with hydrocolloid or hydrogel, so that even when bedsores develop, it can be treated, and the treatment state of the bedsores can be observed with naked eyes by opening the lid 40 of the opening 50 formed at the central portion of the cover layer.

Figure 5:
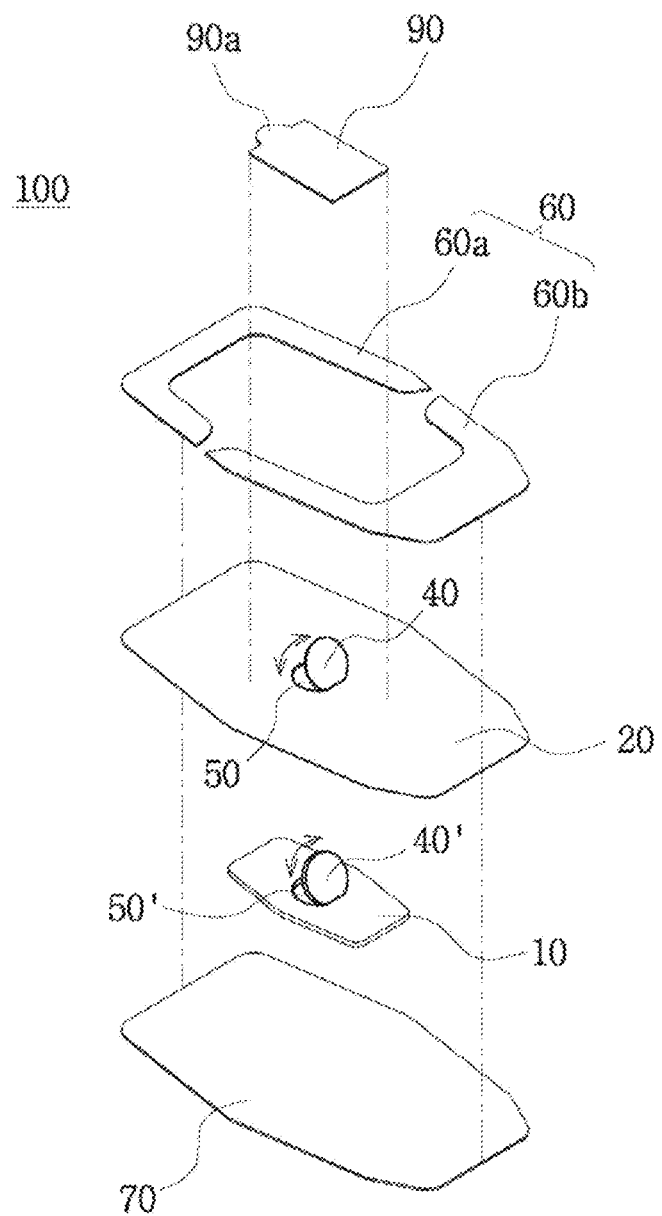
FIG. 5 is an exploded perspective view showing a modified member for preventing bedsores according to a preferred embodiment of the present invention.
Figure 6:
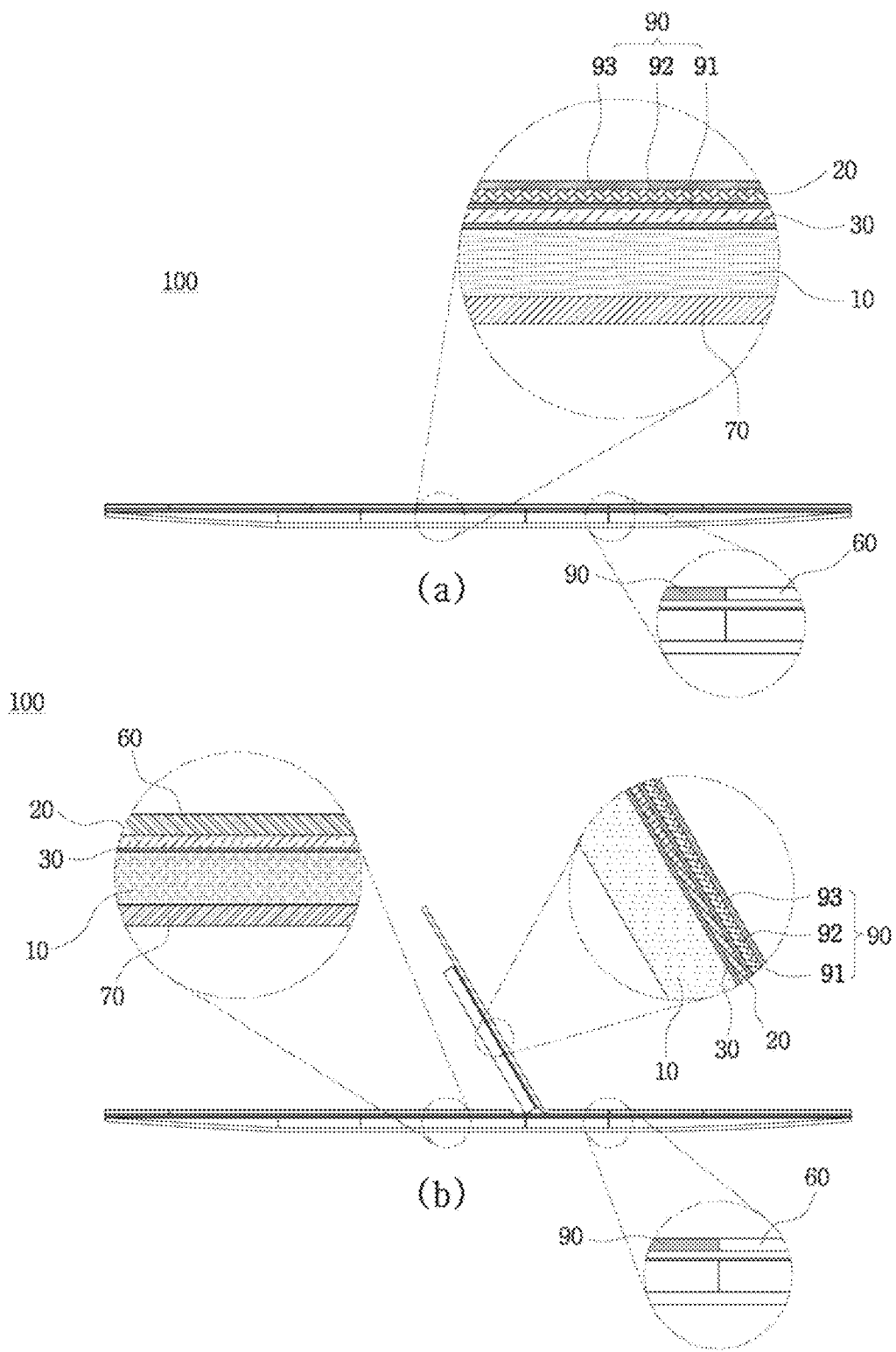
FIG. 6 is a side view showing the modified member for preventing bedsores shown in FIG. 5.
Figure 7:
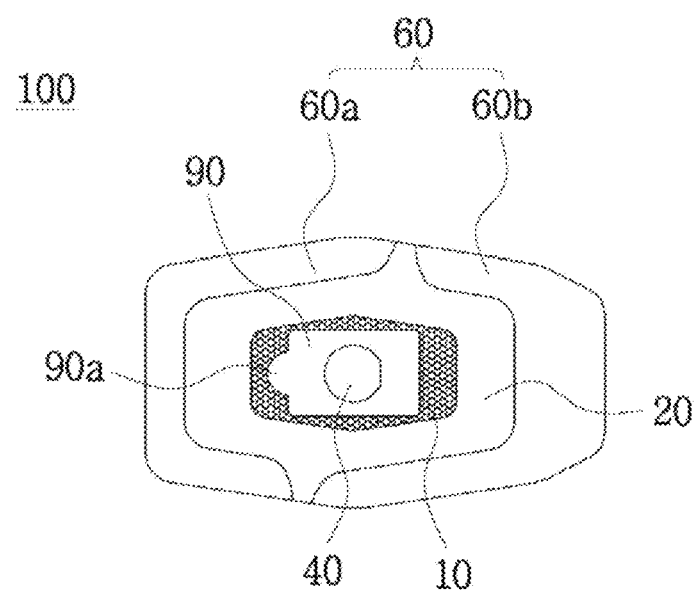
FIG. 7 is a top plan view showing the modified member for preventing bedsores shown in FIG. 5.
Figure 8:
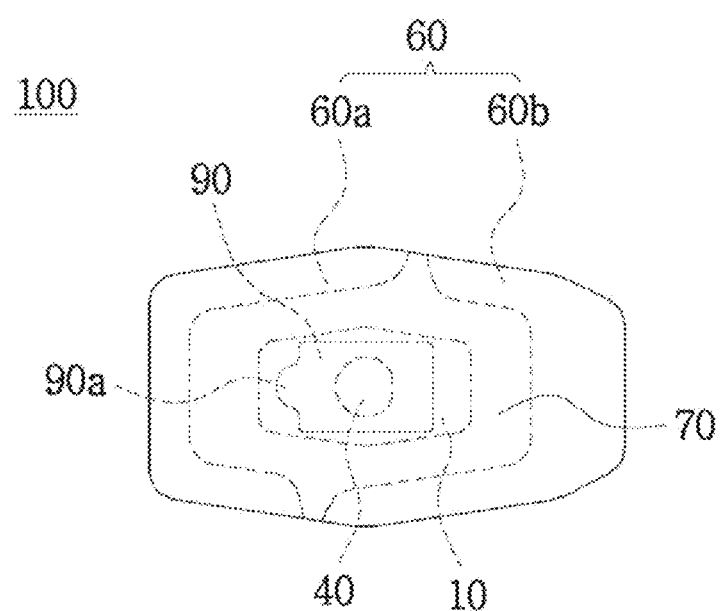
FIG. 8 is a bottom plan view showing the modified member for preventing bedsores shown in FIG. 5.

Further, the cover layer 20 is a layer that is made of a synthetic resin film, which is integrally stacked on the outer surface of the pad layer 10 as shown in FIGS. 5 to 7. The cover layer 20 has a structure in which the pad layer 10 of a synthetic resin film formed in a sheet type from synthetic resin foam and hydrocolloid or hydrogel is immobilized and the remaining peripheral portion of the cover layer 20 other than a portion of the cover layer 20, which corresponds to the pad layer 10, is closely adhered to the patient's skin.

Thus, the cover layer 20 has a structure in which it has a length and width larger than that of the pad layer 10, and is stacked on the pad layer 10 in such a manner that the pad layer 10 is positioned around the central portion of the cover layer 20 as shown in FIG. 7. By virtue of this structure, even when the patient excretes urine and feces in a disposable diaper 80, the excrement can be prevented from permeating the patient's skin site where bedsore is apt to occur by means of the cover layer 20 adhered to the patient's skin.

A material for the cover layer 20 that can be used in the present invention may be various synthetic resin materials such as polyurethane, polyethylene and polypropylene, but is most preferably polyurethane.

In addition, the cover layer 20 may be used by coating a medication having a bactericidal activity such as an iodine compound on the inner surface or the inner and outer surfaces of the synthetic resin film constituting the cover layer 20 in order to impart the bactericidal and therapeutic effect to an affected part of the skin.

The pressure-sensitive adhesive layer 30 is a layer that is formed on the inner surface of the cover layer 20 and has a pressure sensitive adhesive applied thereon, and serves to allow the cover layer 20 to be adhered to the patient's skin. The pressure-sensitive adhesive that can be used in the present invention is preferably a polyurethane-based pressure sensitive adhesive which is harmless to the human body.

In the meantime, the modified member 100 for preventing bedsores according to the present invention has a structure in which the pad layer 10 of a synthetic resin film formed in a sheet type from synthetic resin foam and hydrocolloid or hydrogel and the cover layer 20 of a synthetic resin film are stacked on top of each other to form a stacked body, and the opening 50 is formed at the central portion of the cover layer 20 so that the lid 40 coupled integrally with the pad layer 10, the pressure-sensitive adhesive layer 30 and the cover layer 20 can be opened/closed relative to the opening 50 with the lid 40 coupled integrally with the opening 50. The lid cover 90 has a structure in which the pressure-sensitive adhesive layer 91, the release material layer 92, and the protective layer 93 are stacked upwards in order, so that the release material layer 92 is adhered to the cover layer 20 that is an upper layer of the stacked body by means of the pressure-sensitive adhesive layer 91 of the lid cover 90. The lid cover 90 has a structure of including a knob 90a formed at one side or both sides thereof to facilitate the opening/closing of the lid 40 relative to the opening 50. Thus, when the modified member for preventing bedsores is adhered to the patient's skin and then a skin site where bedsores are apt to occur or a skin site where bedsores occurred is observed, the lid 40 covering the opening 50 is easily opened by lifting the knob 90a of the lid cover 90 without completely separating the modified member for preventing bedsores from the patient's skin site to allow an affected site of the skin to be observed with naked eyes, and then the lid 40 is easily closed relative to the opening 50 by press-fit engagement after lowering the knob 90a of the lid cover 90 to its original position.

In addition, the modified member 100 for preventing bedsores according to the present invention is configured such that the opening 50 is formed at the central portion of the cover layer of the stacked body to allow the lid 40 to be opened/closed relative to the opening 50. Thus, according to the present invention, in addition to the use of the modified member for prevention of bedsores, even in the treatment of skin trauma such as common wounds and burns, the treatment state of the skin trauma can be observed with naked eyes by opening the lid of the opening formed at the central portion of the cover layer using the modified member so that the frequency of unnecessary treatments can be reduced, and only the opening/closing element (i.e., the lid) can be easily replaced with new one without completely removing the modified member so that the use of the member for medical treatment can be reduced, thereby ensuring economic efficiency.

In addition, the modified member 100 for preventing bedsores includes either an upper release paper 60 and a lower release paper 70, which are respectively stacked on both outer surfaces thereof, or the lower release paper (70) stacked on one outer surface thereof.

The upper release paper 60 includes one-half upper release paper 60a and the other-half upper release paper 60b, which are separately stacked on a peripheral portion of the outer surface of the cover layer 20 and have a shape similar to that of a horseshoe. The aim at forming the two half upper release papers in a horseshoe shape is to facilitate attachment is to easily attach the two half upper release papers to the outer surface of the cover layer 20 by holding the horseshoe parts having a larger width with hands while directly watching the upper release paper with naked eyes.

The lower release paper 70 is a release paper that has the same shape as that of the cover layer 20 to correspond in shape to the cover layer 20. The aim at forming the lower release paper 70 is to prevent the modified member 100 for preventing bedsores from being contaminated by external bacteria. The lower release paper 70 is stacked on the inner surface of the cover layer 20.

Hereinafter, the operation of the modified member for preventing bedsores according to a preferred embodiment of the present invention will be described in more detail with reference to examples, but the scope of the present invention is necessarily not limited by these examples.

Figure 9:
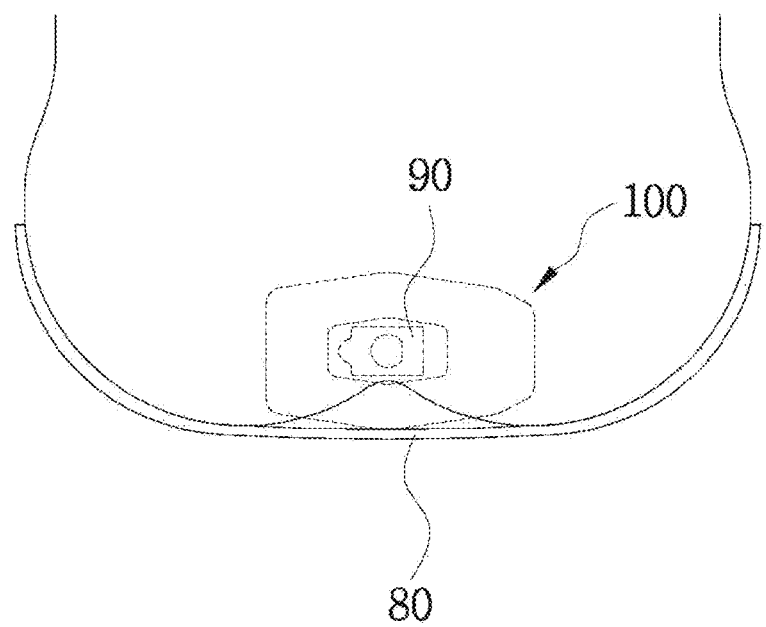
FIG. 9 is a schematic view showing a use state of a modified member for preventing bedsores according to a preferred embodiment of the present invention.

As shown in FIG. 9, when it is desired to adhere the modified member 100 for preventing bedsores to a patient's skin, the lower release paper 70 is first removed from the stacked body and then the modified member 100 for preventing bedsores is adhered to the patient's skin site (for example, a skin site between the central part of the buttock and the anus and bilateral femoral puncture sites where bedsore is apt to occur) where bedsore occurred or is apt to occur. Thereafter, the upper release paper 60 is removed from the stacked body and then a disposable diaper 80 is worn on the patient's body.

Thus, the modified member 100 for preventing bedsores according to the present invention is configured such that a patient's excrement such as urine and feces excreted in a disposable diaper does not permeate a skin site between the central part of the buttock and the anus and bilateral femoral puncture sites where bedsore is apt to occur by means of the modified member 100, thereby preventing the development of bedsores.

While the modified member for preventing bedsores according to the present invention has been described and illustrated in connection with specific exemplary embodiments with reference to the accompanying drawings, it will be readily appreciated by those skilled in the art that it is merely illustrative of the preferred embodiments of the present invention, and various modifications and changes can be made thereto within the technical spirit and scope of the present invention.

BEST MODE

In a best mode for carrying out the present invention, the present invention provides a modified member for preventing bedsores, which includes a stacked body composed of: a pad layer 10 of a synthetic resin film formed in a sheet type from synthetic resin foam and hydrocolloid or hydrogel, so as to come into direct contact with a patient's skin; a cover layer 20 of a synthetic resin film, which is integrally stacked on the outer surface of the pad layer 10; and a pressure-sensitive adhesive layer 30 formed on the inner surface of the cover layer 20 and having a pressure-sensitive adhesive applied thereon;. The cover layer 20 includes an opening 50 penetratingly formed at a central portion thereof to allow an affected part of the patient's skin to be observed with naked eyes therethrough. The modified member 100 further includes a lid 40 disposed at the opening to correspond to the shape of the opening 50 so that the lid can be opened/closed relative to the opening 50 by press-fit engagement; and a lid cover 90 disposed on the upper outer surface of the lid 40 and having an area larger than that of the lid.

INDUSTRIAL APPLICABILITY

The modified member for preventing bedsores according to the present invention is expected to be industrially applicable since it includes a lid cover disposed on the upper outer surface of the lid and having an area larger than that of the lid so that in addition to the use of the modified member for prevention of bedsores, even in the treatment of skin trauma such as common wounds and burns, the treatment state of the skin trauma can be observed with naked eyes by opening the lid of the opening formed at the central portion of the cover layer using the modified member so that the frequency of unnecessary treatments can be reduced, and only the opening/closing element (i.e., the lid) can be easily replaced with new one without completely removing the modified member so that the use of the member for medical treatment can be reduced, thereby ensuring economic efficiency.

The invention claimed is:

1. A modified member for preventing bedsores with a lid cover (90), which comprises a stacked body composed of: a pad layer (10) of a synthetic resin film formed in a sheet type from synthetic resin foam and hydrocolloid or hydrogel, so as to come into direct contact with a skin of a patient; a cover layer (20) of a synthetic resin film, which is integrally stacked on an outer surface of the pad layer (10); and a pressure-sensitive adhesive layer (30) formed on an inner surface of the cover layer (20) and having a pressure-sensitive adhesive applied thereon,
   wherein a length and width of the cover layer (20) is larger than a length and width of the pad layer (10), and the cover layer (20) is stacked on the pad layer (10) in such a manner that the pad layer (10) is positioned around the central portion of the cover layer (20),
   wherein the cover layer (20) comprises an opening (50) penetratingly formed at a central portion thereof and configured to allow an affected part of the skin of the patient to be observed with naked eyes therethrough,
   wherein the modified member for preventing bedsores with the lid cover (90) further comprises; a lid (40) disposed at the opening to correspond to the shape of the opening (50) so that the lid can be opened/closed relative to the opening (50) by press-fit engagement; and the lid cover (90) disposed on an upper outer surface of the lid (40) and having an area larger than an area of the lid,
   wherein the lid cover (90) comprises a structure in which a pressure-sensitive adhesive layer (91), a release material layer (92) selected from among a nonwoven fabric, a natural fiber fabric, a synthetic fiber fabric, a natural rubber material, and a synthetic rubber material, and a protective layer (93) are stacked upwards in order, so that the release material layer (92) is adhered to the cover layer (20) that is an upper layer of the stacked body by means of the pressure-sensitive adhesive layer (91) of the lid cover (90), wherein the protective layer (93) is selected from polyurethane, polyethylene, or polypropylene, and
   wherein the lid cover (90) includes a knob (90a) formed at one side to facilitate the opening/closing of the lid (40) relative to the opening so that the lid (40) is opened by lifting the knob (90a) of the lid cover (90) without completely separating the modified member for preventing bedsores from the skin of the patient, and the lid (40) is closed by press-fit engagement after lowering the knob (90a) of the lid cover (90) to its original position.

2. The modified member for preventing bedsores with the lid cover (90) according to claim 1, wherein the pad layer (10) is obtained by impregnating synthetic resin foam with hydrocolloid or hydrogel.

3. The modified member for preventing bedsores with the lid cover (90) according to claim 1, wherein the modified member for preventing bedsores with the lid cover (90) comprises either an upper release paper (60) and a lower release paper (70), which are respectively stacked on both outer surfaces thereof, or the lower release paper (70) stacked on one outer surface thereof.

\* \* \* \* \*